(12) United States Patent
Tincher

(10) Patent No.: US 10,591,411 B1
(45) Date of Patent: Mar. 17, 2020

(54) WIDEBAND OPTICAL SENSOR AND USE THEREOF IN DISPENSING SYSTEMS

(71) Applicant: Delaware Capital Formation, Inc., Wilmington, DE (US)

(72) Inventor: Terry Tincher, Lebanon, OH (US)

(73) Assignee: Delaware Capital Formation, Inc., Wilmington, DE (US)

( * ) Notice: Subject to any disclaimer, the term of this patent is extended or adjusted under 35 U.S.C. 154(b) by 0 days.

(21) Appl. No.: 16/252,749

(22) Filed: Jan. 21, 2019

(51) Int. Cl.
  *G01N 21/31* (2006.01)
  *G01N 21/25* (2006.01)
(52) U.S. Cl.
  CPC ....... *G01N 21/3151* (2013.01); *G01N 21/255* (2013.01); *G01N 2201/12746* (2013.01)
(58) Field of Classification Search
  CPC ............. G01N 21/3151; G01N 21/255; G01N 2201/12746
  USPC .... 356/432–448, 237.1–237.6, 239.1–239.8, 356/213–236
  See application file for complete search history.

(56) References Cited

U.S. PATENT DOCUMENTS

| | | | |
|---|---|---|---|
| 2012/0218553 A1* | 8/2012 | Fey | B41F 33/0054 356/440 |
| 2015/0346092 A1* | 12/2015 | Lee | G01N 21/314 356/39 |
| 2016/0205995 A1* | 7/2016 | White | G01N 21/3151 |

\* cited by examiner

*Primary Examiner* — Tri T Ton
(74) *Attorney, Agent, or Firm* — Wood Herron & Evans LLP

(57) ABSTRACT

Apparatuses, methods, and software products for analyzing liquids dispensed from a chemical dispensing system. Beams of light having different wavelengths are passed through a liquid dispensed by the dispensing system. The intensity of each beam of light is measured after passing through the liquid. A transmission coefficient is determined by comparing the intensity of the beam of light to a calibration parameter obtained by passing the beam of light through an unadulterated diluent. The transmission coefficients for the beams of light are then compared to corresponding transmission coefficients obtained for one or more known reference solutions to determine one or more characteristics of the liquid being dispensed from the chemical dispensing system.

17 Claims, 10 Drawing Sheets

WIDEBAND OPTICAL SENSOR AND USE THEREOF IN DISPENSING SYSTEMS

BACKGROUND

The invention generally relates chemical dispensing systems, and in particular, to systems, methods, and software products for analyzing solutions dispensed by a chemical dispensing system.

The dispensing of liquid chemical products from one or more chemical receptacles is a common requirement of many industries, such as the ware-wash, laundry, animal health, and food and beverage industries. For example, in an industrial laundry facility, each of several washing machines must be provided with aqueous solutions containing various quantities of alkaloid, detergent, bleach, starch, softener, and/or other chemical products. Dispensing improper amounts of these chemical products may reduce the effectiveness of the washing process. Moreover, in certain operating environments, the amount of chemicals dispensed by the dispenser must be verified to ensure compliance with regulations. For example, health departments may require that solutions used for sanitation in the healthcare and food preparation industries contain a minimum level of a chemical disinfectant.

To ensure proper amounts of chemical products are being delivered to the machines by a chemical dispensing system, monitoring systems have been developed that monitor the flow of product to the machines. These systems typically rely on electrical sensors that require conductive probes which are in contact with the chemical solutions. The conductive probes are thus subject to corrosion and the buildup of deposits that can affect measurement accuracy. Electrical conductivity measurements also tend to be unreliable due to different products having similar electrochemical characteristics and due to unpredictable interactions between chemical products and different impurities in the water provided by different municipal sources. In some cases, adding a small amount of chemical product to a diluent simply fails to change the electrical conductivity of the resulting solution sufficiently to provide an accurate measurement.

Unreliable monitoring systems may result in the machines attached to the chemical dispensing system running without the required amounts of the chemical products. Thus, the performance of the machines may be adversely affected due to too little or too much of the product being dispensed. This may reduce the quality of a machine's output and/or increase expenses by wasting chemical product or requiring items to be re-processed.

Conventional chemical dispensing systems also do not provide a positive confirmation that the system provided the precise amount of chemical called for by the dispensing program. Moreover, it is often difficult to directly measure the precise concentration of chemical product in the solution being dispensed. Thus, dispensing systems are often unable to consistently maintain the required concentrations of chemical solutions for many applications. Systems that monitor the amount of chemical product dispensed, such as by logging pump run, solenoid activation, or dispense times at the system controller, typically do not satisfy compliance monitoring requirements. This is due to the possibility that merely monitoring operation of the dispenser does not ensure the type and percentage of chemicals in the solution being dispensed by the dispensing system. For example, changes in water pressure, chemical product or water leaks, out of product conditions, or other variations in the dispensing system may cause the concentration of chemicals in the solution to be different than would be expected based solely the amount of chemical dispensed.

Therefore, there is a need for improved apparatuses, methods, and software products for monitoring the delivery of chemical products in chemical dispensing systems.

SUMMARY

In an embodiment of the invention, an apparatus for analyzing a liquid is provided. The apparatus includes a holder including a space, one or more photodetectors coupled to the holder, a first light source coupled to the holder, and a second light source coupled to the holder. The first light source is configured to generate a first beam of light that has a first wavelength, passes through the space, and illuminates at least one of the one or more photodetectors after passing through the space. The second light source is configured to generate a second beam of light that has a second wavelength different from the first wavelength, passes through the space, and illuminates at least one of the one or more photodetectors after passing through the space.

In an aspect of the invention, the apparatus may include a chamber positioned in the space and configured to receive the liquid so that the first and second beams of light pass through the liquid in the chamber.

In another aspect of the invention, the chamber may include at least a portion of a machine supply line.

In another aspect of the invention, the chamber may include a connector configured to couple the chamber to the machine supply line.

In another aspect of the invention, the apparatus may include a processor and a memory storing program code. When executed by the processor, the program code may cause the apparatus to receive a first signal from the one or more photodetectors indicative of a first intensity of the first beam of light, receive a second signal from the one or more photodetectors indicative of a second intensity of the second beam of light, determine a first transmission coefficient based on the first intensity, and determine a second transmission coefficient based on the second intensity.

In another aspect of the invention, the program code may cause the apparatus to sequentially activate the first light source and the second light source. The first signal may be received in response to activating the first light source, and the second signal may be received in response to activating the second light source.

In another aspect of the invention, the program code may cause the apparatus to determine a characteristic of the liquid based on the first and second transmission coefficients.

In another aspect of the invention, the characteristic of the liquid may be a type of a chemical product in the liquid, a concentration of the chemical product in the liquid, or both the type and the concentration of the chemical product in the liquid.

In another aspect of the invention, the first and second transmission coefficients may be determined when the liquid is a working solution, and the program code may cause the apparatus to, when the liquid is a reference solution having a known characteristic, receive a third signal indicative of a third intensity of the first beam of light and a fourth signal indicative of a fourth intensity of the second beam of light. The program code may further cause the apparatus to determine a third transmission coefficient based on the third intensity, determine a fourth transmission coefficient based on the fourth intensity, and store the third and fourth transmission coefficients in the memory as chemical calibration parameters. The characteristic of the working solution may then be determined by determining a first difference between the first transmission coefficient and the third transmission coefficient, determining a second difference between the second transmission coefficient and the fourth transmission coefficient, and then determining the characteristic of the working solution based on the known characteristic, the first difference, and the second difference.

In another aspect of the invention, the first and second transmission coefficients may be determined when the liquid is one of a working solution or a reference solution, and the program code may further cause the apparatus to, when the liquid is an unadulterated diluent, receive a third signal indicative of a third intensity of the first beam of light, and receive a fourth signal indicative of a fourth intensity of the second beam of light. The program code may further cause the apparatus to store the third intensity as a first baseline calibration parameter in the memory, and store the fourth intensity as a second baseline calibration parameter in the memory. The first transmission coefficient may be determined by comparing the first intensity to the first baseline calibration parameter, and the second transmission coefficient may be determined by comparing the second intensity to the second baseline calibration parameter.

In another embodiment of the invention, a method of analyzing the liquid is provided. The method includes passing the first beam of light having the first wavelength through the liquid, measuring the first intensity of the first beam of light after passing through the liquid, passing the second beam of light having the second wavelength different from the first wavelength through the liquid, measuring the second intensity of the second beam of light after passing through the liquid, and determining the characteristic of the liquid based on the first intensity and the second intensity.

In another aspect of the invention, the method may include determining the first transmission coefficient based on the first intensity, and determining the second transmission coefficient based on the second intensity. The characteristic of the liquid may then be determined based on the first transmission coefficient and the second transmission coefficient.

In another aspect of the invention, the first and second transmission coefficients may be determined when the liquid is a working solution, and method may include passing the first beam of light through the reference solution having the known characteristic, measuring the third intensity of the first beam of light after passing through the reference solution, determining the third transmission coefficient based on the third intensity, passing the second beam of light through the reference solution, measuring the fourth intensity of the second beam of light after passing through the reference solution, and determining the fourth transmission coefficient based on the fourth intensity. In this aspect of the invention, determining the characteristic of the working solution may include determining the first difference between the first transmission coefficient and the third transmission coefficient, determining the second difference between the second transmission coefficient and the fourth transmission coefficient, and determining the characteristic of the working solution based on the known characteristic, the first difference, and the second difference.

In another aspect of the invention, the method may include storing the third and fourth transmission coefficients in the memory as the chemical calibration parameters.

In another aspect of the invention, the first and second intensities may be determined when the liquid is one of the working solution or the reference solution, and the method may include, when the liquid is the unadulterated diluent, determining the third intensity of the first beam of light, setting the first baseline calibration parameter equal to the third intensity, determining the fourth intensity of the second beam of light, setting the second baseline calibration parameter to the fourth intensity, determining the first transmission coefficient by comparing the first intensity to the first baseline calibration parameter, and determining the second transmission coefficient by comparing the second intensity to the second baseline calibration parameter. The characteristic of the liquid may then be determined based on the first and second transmission coefficients.

In another aspect of the invention, the first intensity and the second intensity may be measured using a single photodetector.

In another aspect of the invention, the first beam of light and the second beam of light may be passed through the liquid sequentially.

In another aspect of the invention, the method may include receiving the liquid in the chamber, and the first beam of light and the second beam of light may be passed through the liquid in the chamber.

In another embodiment of the invention, a computer program product for analyzing the liquid is provided. The computer program product includes a non-transitory computer-readable storage medium, and program code stored on the non-transitory computer-readable storage medium. The program code is configured to, when executed by one or more processors, cause the one or more processors to pass the first beam of light having the first wavelength through the liquid, measure the first intensity of the first beam of light after the first beam of light has passed through the liquid, pass the second beam of light having the second wavelength different from the first wavelength through the liquid, measure the second intensity of the second beam of light after the second beam of light has passed through the liquid, and determine the characteristic of the liquid based on the first intensity and the second intensity.

The above summary may present a simplified overview of some embodiments of the invention to provide a basic understanding of certain aspects the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

DETAILED DESCRIPTION

Embodiments of the invention are directed to systems, methods, and software products for analyzing solutions dispensed by dispensing systems. To this end, a sensor control module in communication with a broadband optical sensor may capture an optical absorption signature of a solution being dispensed by a chemical dispensing system. These solutions typically include a chemical product that is in a diluted state. The optical absorption signature may be used to determine the chemical content of the solution at the output of the dispensing system or a point of use of the solution. Embodiments of the invention may be used to validate the types, amounts, and concentrations of chemical product in the chemical solutions being dispensed, and may be used with different types of dispensing systems, technologies, and operating environments. Using an optical analysis approach may allow the chemical solutions to be characterized while avoiding direct contact with the solutions or the chemical products used to make the solutions. This feature may improve the durability and reliability of embodiments of the invention as compared to systems that rely on other types of sensors, such as electrical conductivity probes. Using a plurality of monochromatic light sources rather than a single broadband light source in combination with a dispersive element may enable embodiments of the invention to provide chemical analyses with accuracies similar to those available using benchtop spectrometers, but in real time and with lower cost and complexity.

Figure 1:
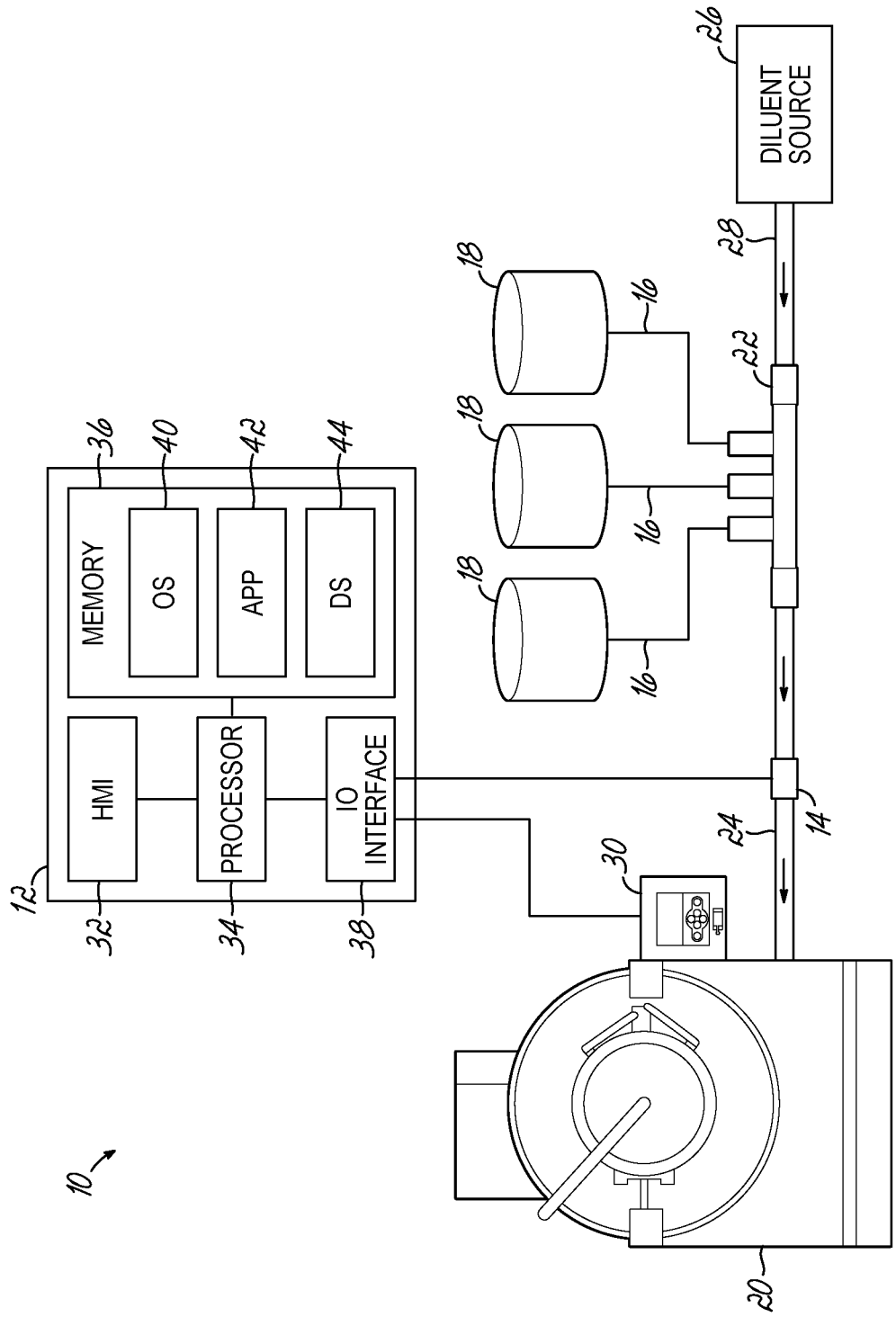
FIG. 1 is a diagrammatic view of an operating environment including a sensor control module and an optical sensor that analyzes a solution provided to a machine by a dispenser.

FIG. 1 depicts an operating environment for an exemplary chemical dispensing system 10 that includes a sensor control module 12 in communication with one or more optical sensors 14. Product supply lines 16 may fluidically couple one or more (e.g., three) sources of chemical product 18 to a machine 20, such as a washing machine, via a dispenser 22 (e.g., a flush manifold). An output of the dispenser 22 may be coupled to the machine 20 by a machine supply line 24, and an input of the dispenser 22 may be coupled to a source of diluent 26, such as a municipal water line, by a diluent supply line 28. Each source may selectively provide its product 18 and/or diluent 26 to the machine 20 in response to signals from a system controller 30. The system controller 30 may thereby control the amount and timing of product 18 and/or diluent 26 provided to the machine 20 by regulating the flow of products 18 and diluent 26 through the dispenser 22. The machine supply line 24 may comprise a tube of optically transparent material, and may couple the output of the dispenser 22 to the machine 20. Examples of tubing that may be suitable for use in the product and machine supply lines include Tygon® tubing, which is available from Saint-Gobain S.A. of Courbevoie, France.

The sensor control module 12 may be separate from or integrated with the optical sensor 14, and may include a Human Machine Interface (HMI) 32, a processor 34, a memory 36, and an input/output (I/O) interface 38. The HMI 32 may include output devices, such as an alphanumeric display, a touch screen, and/or other visual and/or audible indicators that provide information from the processor 34 to a user. The HMI 32 may also include input devices and controls, such as an alphanumeric keyboard, a pointing device, keypads, pushbuttons, control knobs, etc., capable of accepting commands or input from the user and transmitting the entered input to the processor 34.

The processor 34 may include one or more devices configured to manipulate signals (analog or digital) based on operational instructions that are stored in memory 36. Memory 36 may be a single memory device or a plurality of memory devices including but not limited to read-only memory (ROM), random access memory (RAM), volatile memory, non-volatile memory, static random-access memory (SRAM), dynamic random-access memory (DRAM), flash memory, cache memory, or any other device capable of storing information. Memory 36 may also include a mass storage device (not shown), such as a hard drive, optical drive, tape drive, non-volatile solid-state device or any other device capable of storing information.

Processor 34 may operate under the control of an operating system 40 that resides in memory 36. The operating system 40 may manage module resources so that computer program code embodied as one or more computer software applications 42 residing in memory 36 may have instructions executed by the processor 34. In an alternative embodiment, the processor 34 may execute the applications 42 directly, in which case the operating system 40 may be omitted. One or more data structures 44 may also reside in memory 36, and may be used by the processor 34, operating system 40, and/or application 42 to store data.

The I/O interface 38 operatively couples the processor 34 to other components in the dispensing system 10, such as the optical sensor 14 and/or system controller 30. The I/O interface 38 may include signal processing circuits that condition incoming and outgoing signals so that the signals are compatible with both the processor 34 and the components to which the processor 34 is coupled. To this end, the I/O interface 38 may include analog to digital (A/D) and/or digital to analog (D/A) converters, voltage level and/or frequency shifting circuits, optical isolation and/or driver circuits, and/or any other analog or digital circuitry suitable for coupling the processor 34 to the other components of the dispensing system 10.

Figure 2:
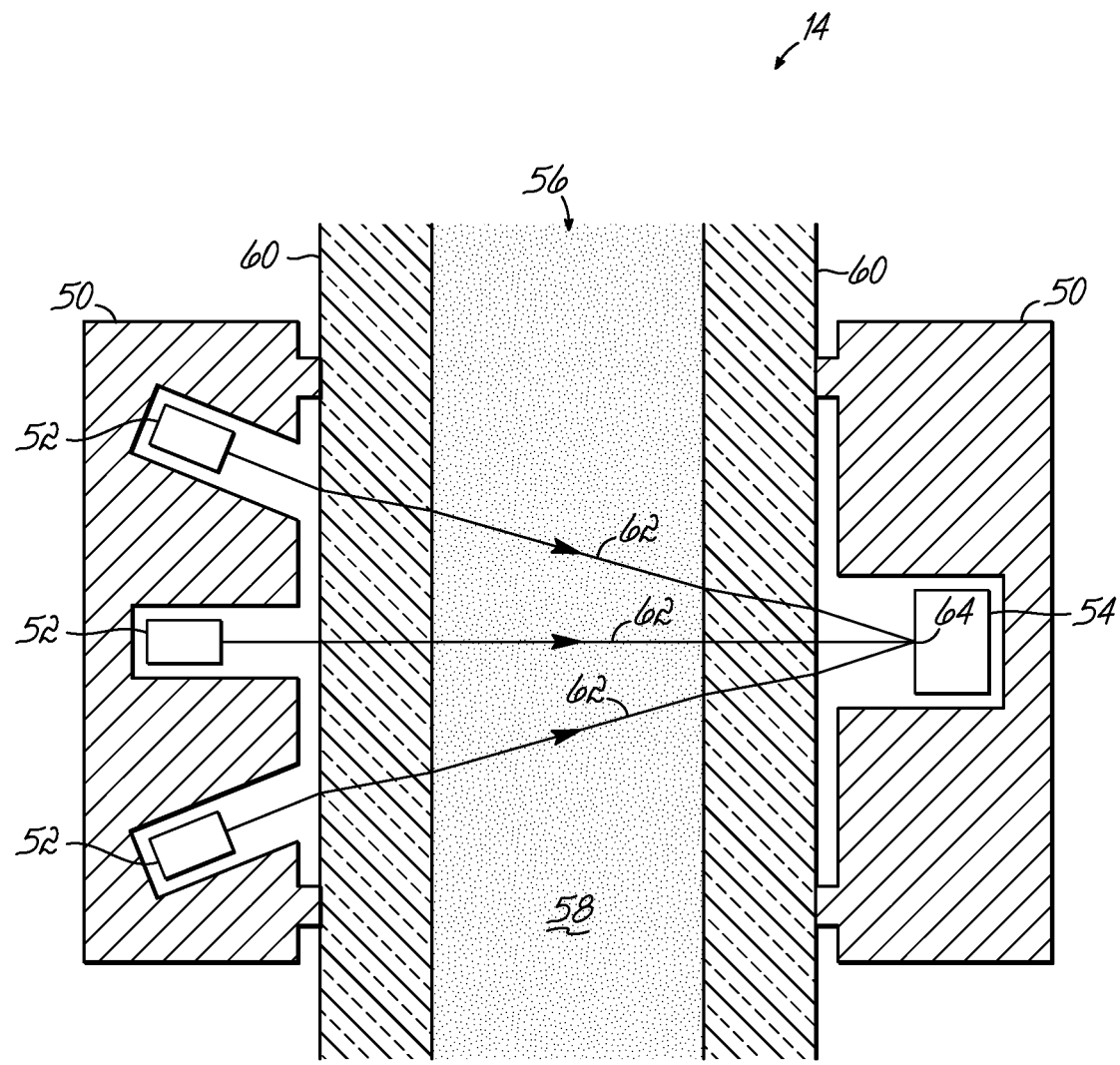
FIGS. 2-4 are diagrammatic views of the optical sensor of FIG. 1 in accordance with embodiments of the invention including a plurality of light sources, a chamber containing the solution, one or more photodetectors, and light beams that originate from the light sources, pass through the solution in the chamber, and illuminate the one or more photodetectors.
Figure 3:
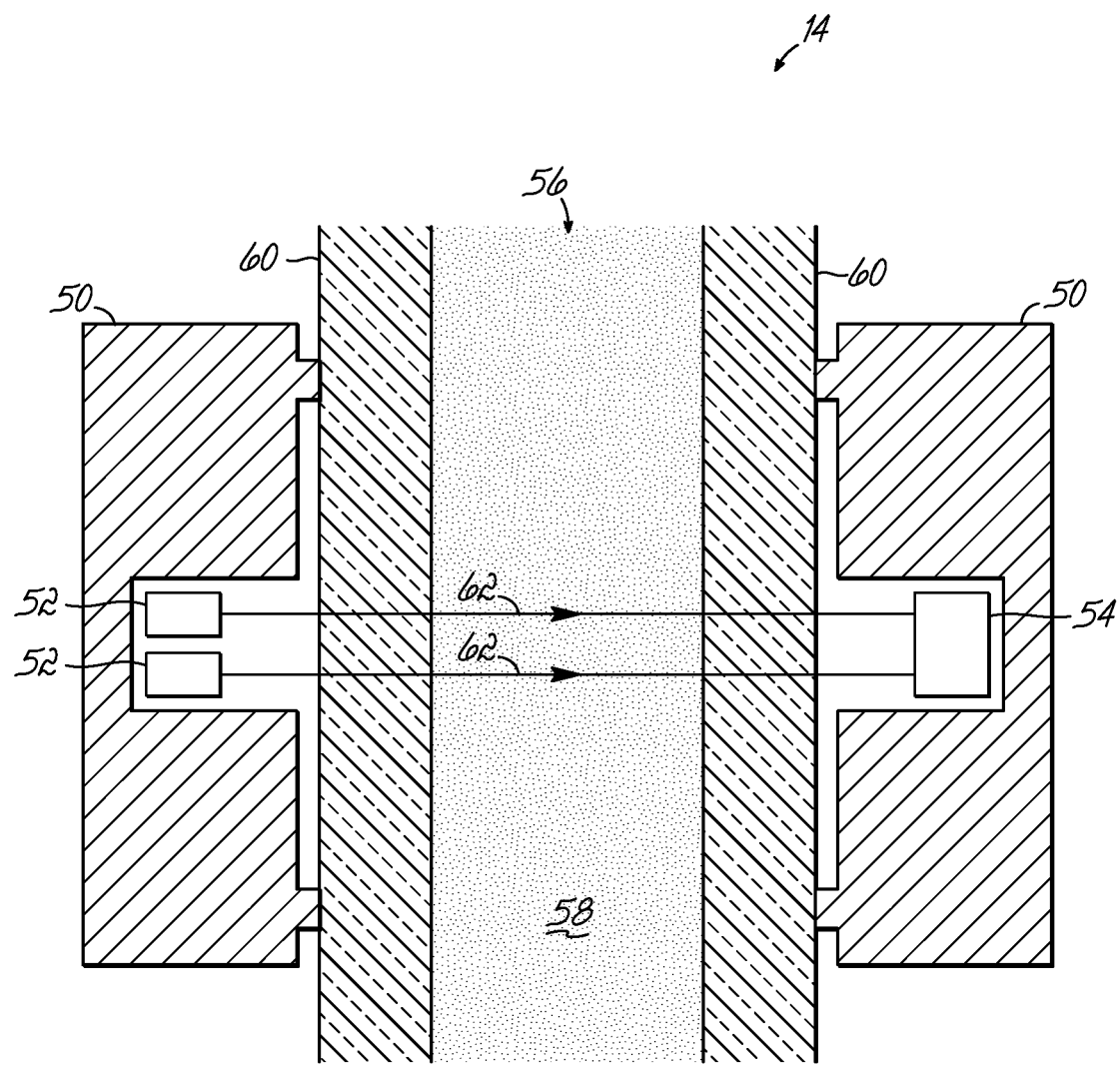
Figure 4:
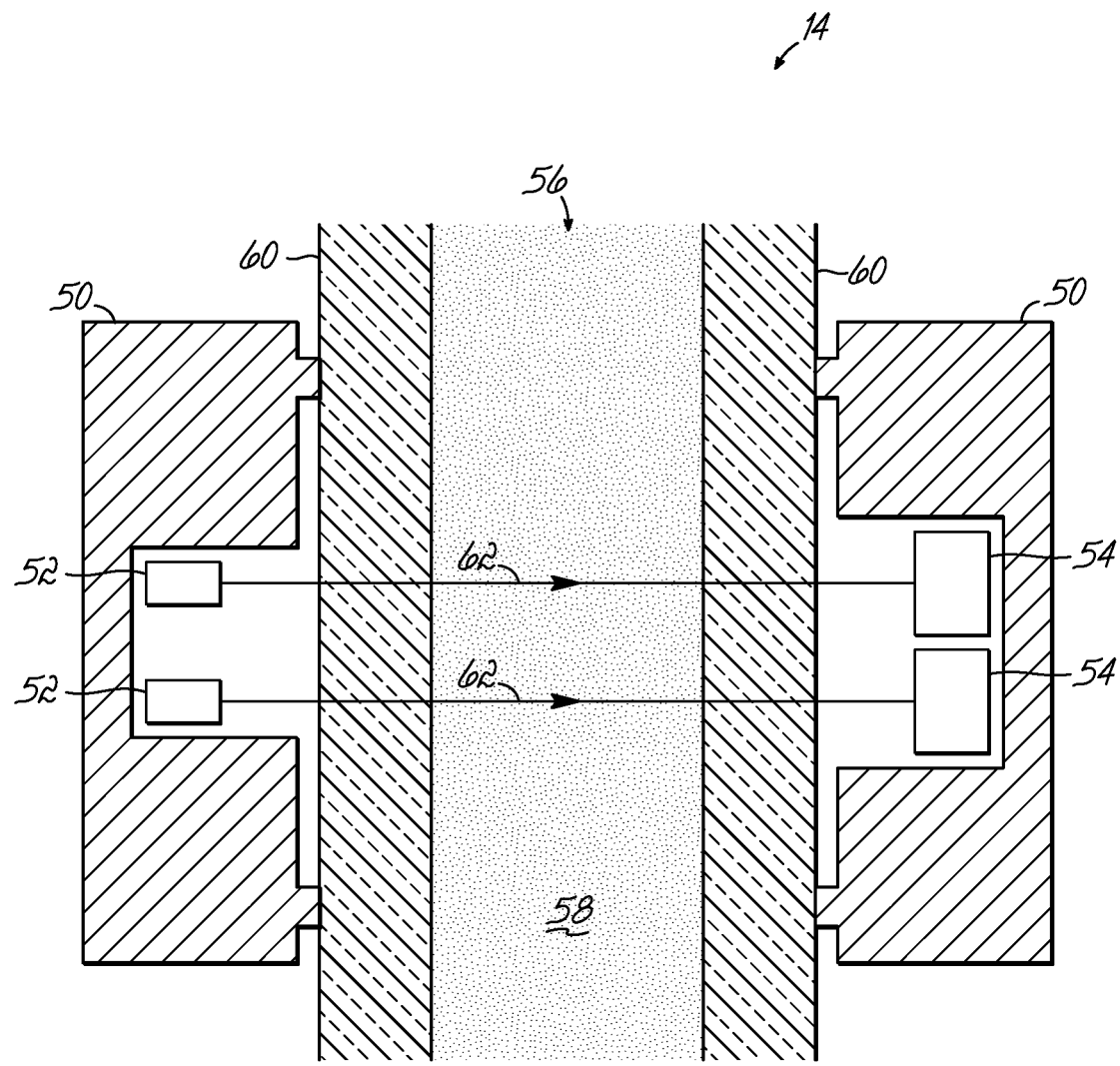
Figure 5:
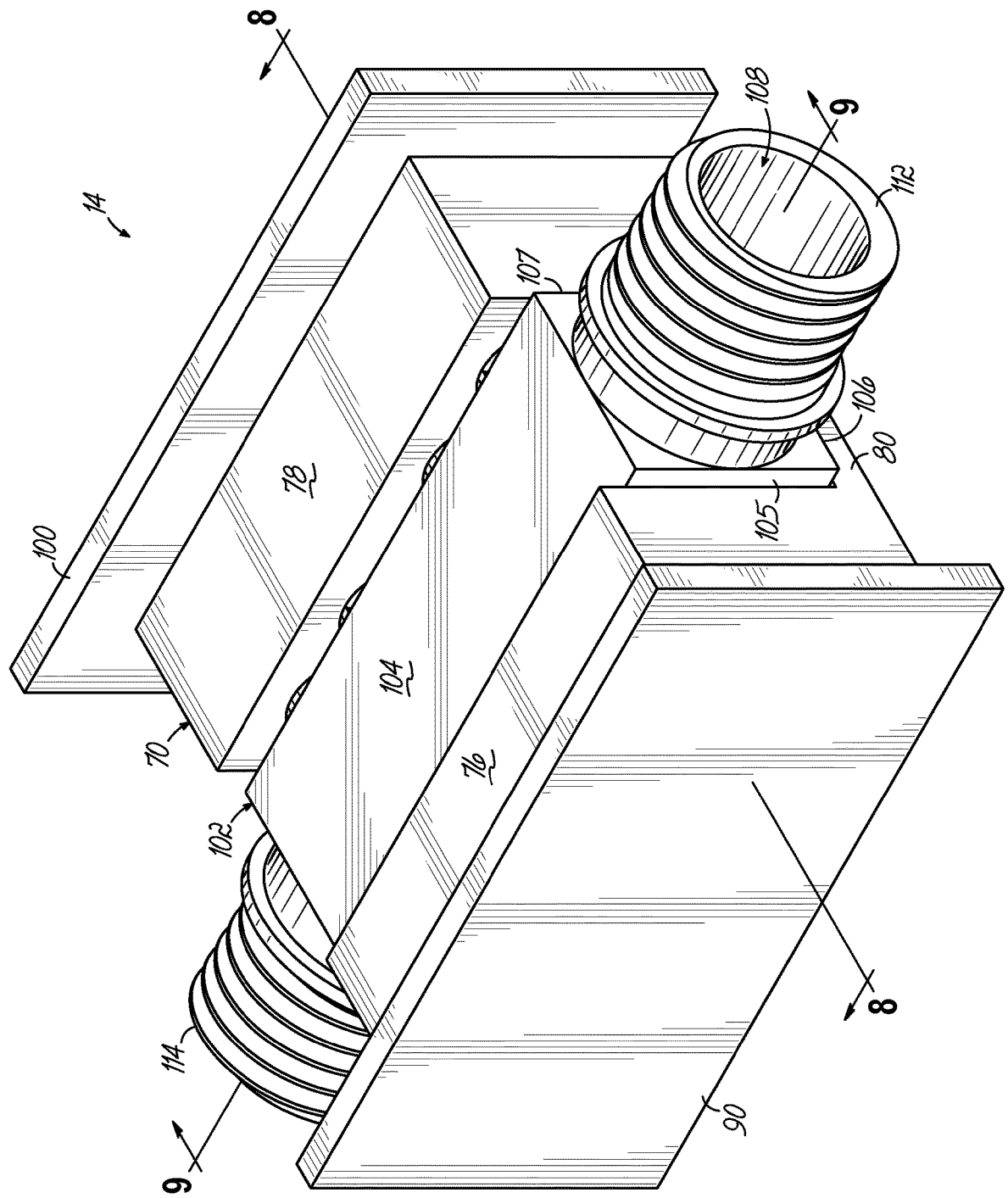
FIG. 5 is an isometric view of an optical sensor in accordance with the optical sensors of FIGS. 1-4 that includes a holder having a plurality of passages which optically couple the light sources and the photodetectors to the solution in the chamber.
Figure 6:
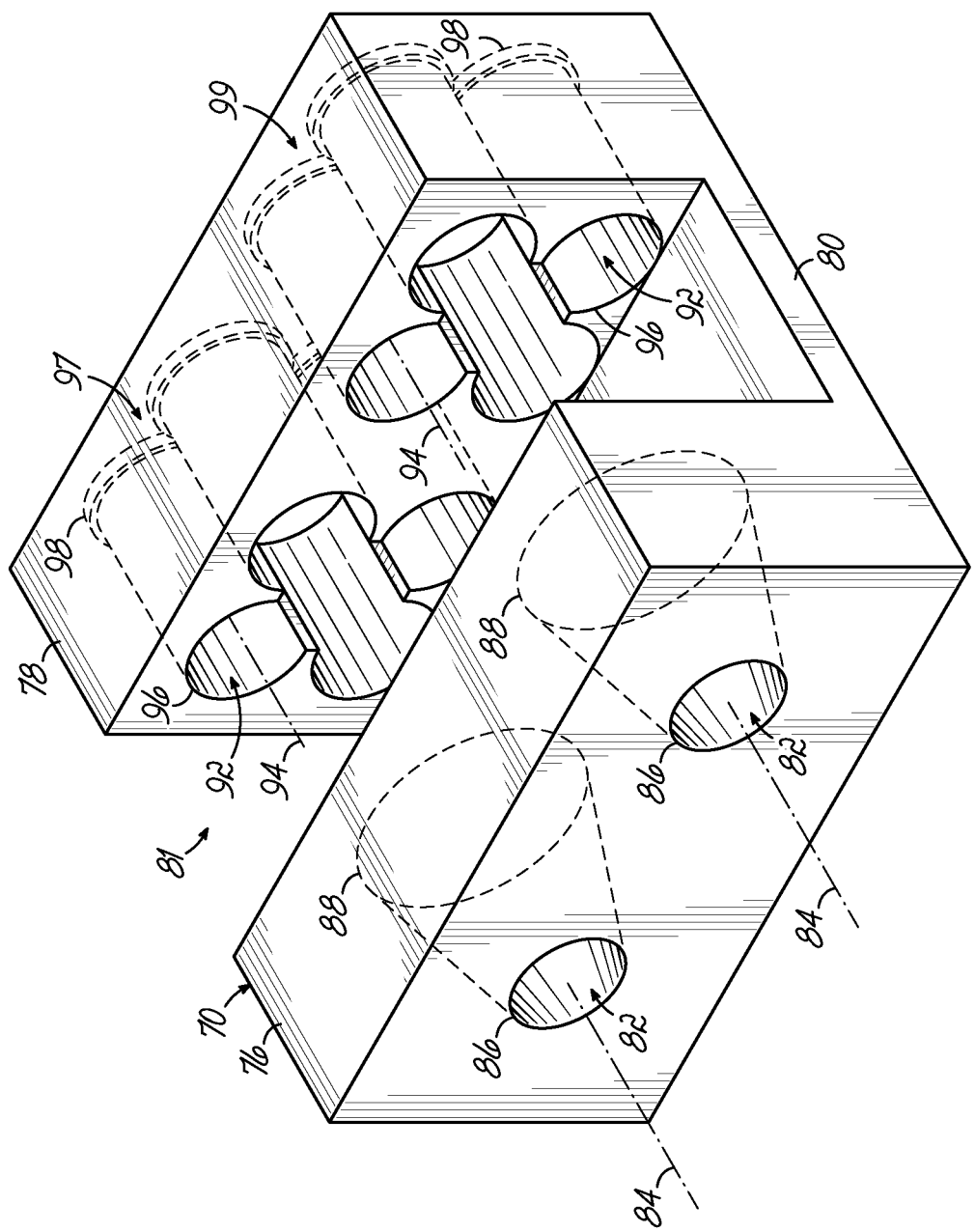
FIG. 6 is isometric view of the holder of the optical sensor of FIG. 5 showing additional details of the passages in the holder.

FIGS. 2-4 depict optical sensors 14 in accordance with one or more embodiments of the invention. Each of the depicted optical sensors 14 includes a holder 50, a plurality of light sources 52, and one or more photodetectors 54. The holder 50 may be configured to locate the light sources 52 and photodetectors 54 in a fixed position relative to a chamber 56 that contains or through which a solution 58 passes. The chamber 56 may include walls 60 defining an interior of chamber 56 that is configured to contain the solution 58. The walls 60 of chamber 56 may be made of any suitable optically transparent material, such as polymethylpentene (also known as PMP or poly(4-methyl-1-pentene)), which is a corrosion resistant thermoplastic polymer of 4-methyl-1-pentene. The chamber 56 may be coupled between sections of the machine supply line 24, or may comprise a portion of the machine supply line 24 itself, so that the chamber 56 is provided with the solution 58 from the dispenser 22. For chambers 56 comprising a portion of the machine supply line 24, the walls 60 of chamber 56 may be provided by the tubing used for the machine supply line 24.

The holder 50 may be configured to provide an optical path for a beam of light 62 emitted by each light source 52 so that each beam of light 62 is incident on or otherwise illuminates one of the one or more photodetectors 54. The beams of light 62 may be relatively narrow and/or have a relatively low divergence (e.g., in the case of a laser diode), or be relatively broad and/or have a relatively high divergence (e.g., in the case of a normal LED). Each light source 52 may be configured to emit a beam of light 62 having a wavelength Α different from at least one of the other light sources 52. The optical sensor 14 may be configured so that more than one beam of light 62 illuminates at least one of the one or more photodetectors 54 (e.g., as shown in FIGS. 2 and 3), or so that one or more of the beams of light 62 illuminate separate photodetectors 54 (e.g., as shown in FIG. 4).

As best shown by FIG. 2, when a beam of light 62 crosses a boundary between one medium and another (e.g., air and wall 60, wall 60 and solution 58, etc.), the optical path of the beam of light 62 may be altered by refraction due to each medium having a different index of refraction. This alteration in the optical path may result in the angle of emission as the beam of light 62 leaves the boundary being different than the angle of incidence of the beam of light 62 as it enters the boundary. The orientation of the sources of light 52 may take into account refraction at the boundaries so that each beam of light 62 is aligned with a single focal point 64 on the photodetector 54 when the chamber 56 is filled with solution 58.

Each of the light sources 52 may comprise an LED that emits the beam of light 62. The beams of light 62 may comprise, for example, blue light (e.g., 460 nm<λ<490 nm), cyan light (e.g., 490 nm<λ<520 nm), green light (e.g., 520 nm<λ<550 nm), chartreuse light (e.g., 550 nm<λ<570 nm), yellow light (e.g., 570 nm<λ<590 nm), orange light (e.g., 590 nm<λ<610 nm), orange-red light (e.g., 610 nm<λ<620 nm), red light (e.g., 620 nm<λ<760 nm), and/or any other suitable wavelength of light in the visible, infrared, and/or ultraviolet ranges of light. The spectral width (e.g., full width at half maximum) of the light sources 52 may vary depending on the type of source. For example, regular colored LED's may have a relatively broad spectral width (e.g., 25 nm), while laser diode LEDs may have a relatively narrow spectral width (e.g., 2 nm).

It has been determined that using eight light sources 52 each having a different wavelength λ to analyze the output of the dispenser 22 provides sufficient spectral resolution for many applications. However, it should be understood that optical sensors 14 having fewer light sources 52 may also be used, and may operate with a reduced spectral resolution as compared to an optical sensor 14 having eight light sources 52. Likewise, optical sensors 14 having more than eight light sources 52 may also be used and operate with a correspondingly increased spectral resolution. The spacing between the wavelengths of the light sources 52 may also be varied, for example, to concentrate spectral resolution in portions of the spectrum that provide optimal results with the products 18 and/or diluent 26 in use.

FIGS. 5-9 depict an optical sensor 14 that includes a holder 70, a plurality of light sources 72 (e.g., eight light sources), and one or more photodetectors 74 (e.g., two photodetectors). The holder 70 may be formed of a solid piece of material (e.g., metal or plastic) and include a detector mounting block 76 operatively connected to a source mounting block 78 by a cross-member 80 so that there is a space 81 between the detector mounting block 76 and source mounting block 78. The detector mounting block 76 may include a plurality of frustoconical passages 82 (e.g., two passages) each having an axis 84, a narrow end 86 facing away from the source mounting block 78, and a wide end 88 facing toward the source mounting block 78. The narrow end 86 of each passage 82 may be configured to receive one of the photodetectors 74, which may be mounted to and held in place by a detector circuit board 90.

The source mounting block 78 may include a plurality of cylindrical passages 92 (e.g., eight passages) each having a diameter $d_1$ and including an axis 94 that is generally parallel to the axes 84 of frustoconical passages 82, a proximal end 96 facing the detector mounting block 76, and a distal end 98 facing away from the detector mounting block 76. The cylindrical passages 92 may be clustered into one or more of groups 97, 99 (e.g., two groups) each including a portion of the plurality of cylindrical passages 92 (e.g., four passages in each group 97, 99).

Figure 7:
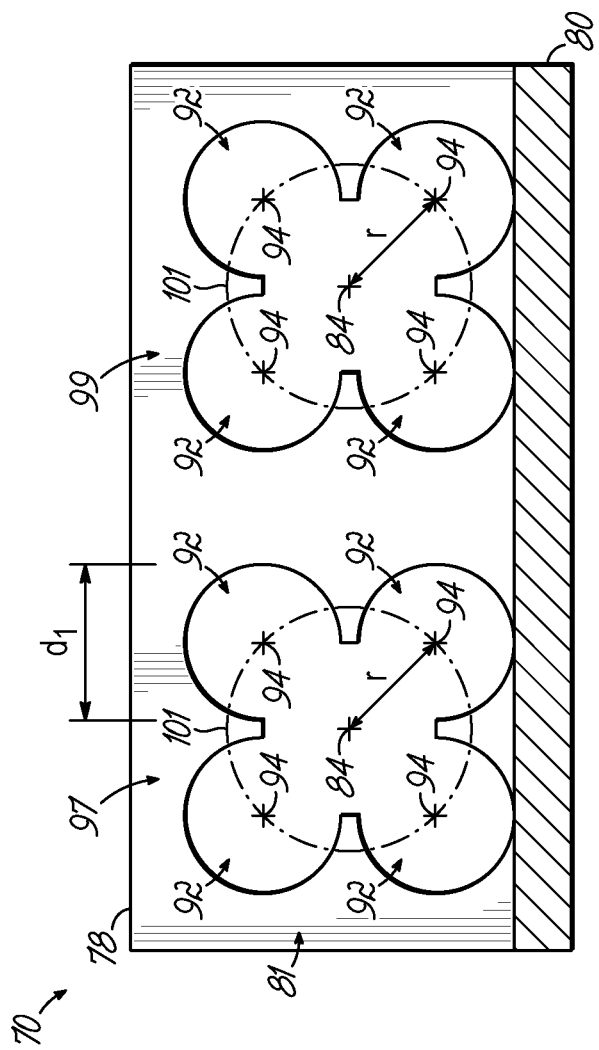
FIG. 7 is a cross-sectional view of the holder of FIG. 5 showing details of the passages that optically couple the light sources to the solution in the chamber.
Figure 8:
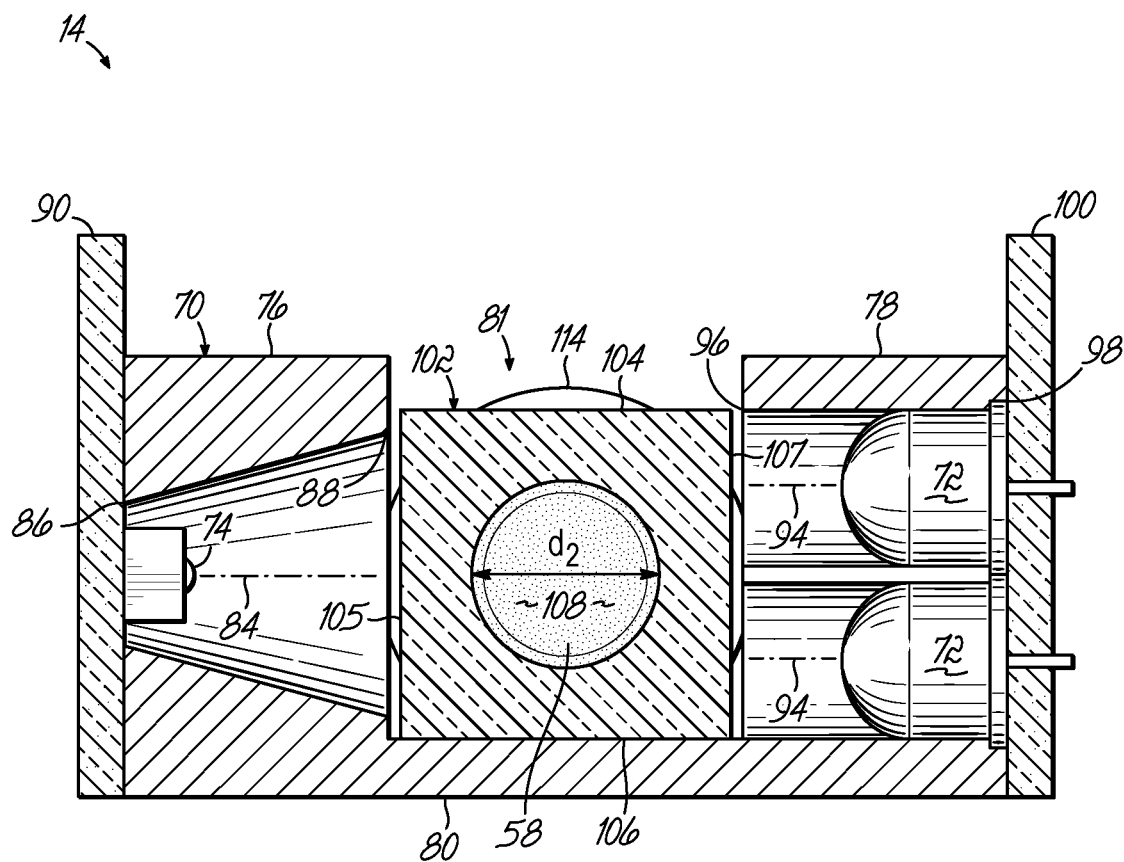
FIG. 8 is another cross-sectional view of the holder and chamber of FIG. 5 showing additional details of the passages that optically couple the light sources and the photodetectors to the solution in the chamber.
Figure 9:
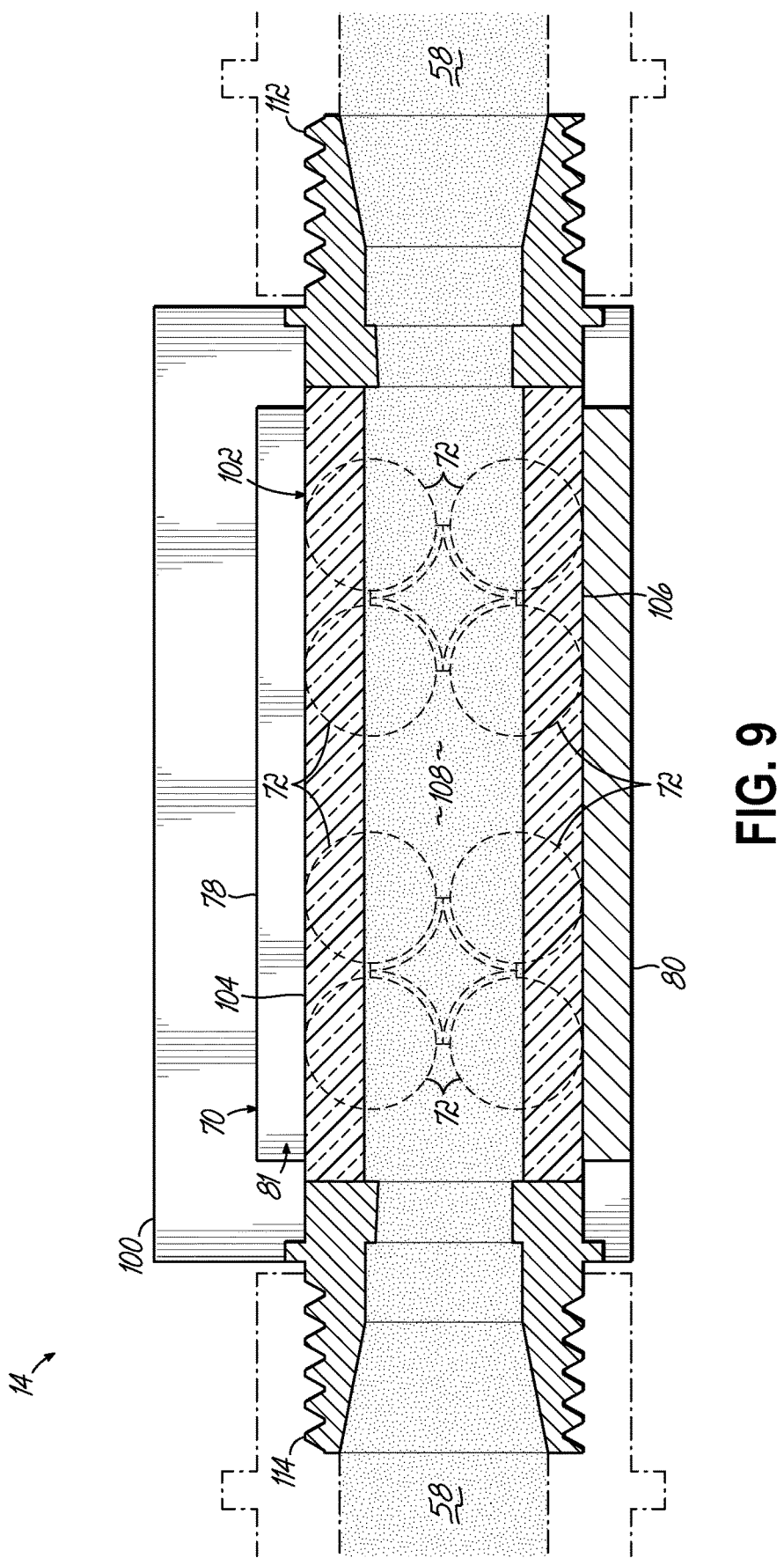
FIG. 9 is a lengthwise cross-sectional view of the holder and chamber of FIG. 8 showing additional details of the chamber.

The cylindrical passages 92 and frustoconical passages 82 may be configured so that at least a portion of a beam of light emitted from the proximal ends 96 of the passages 92 will illuminate one of the photodetectors 74. To this end, the holder 70 may be configured so that each group 97, 99 of cylindrical passages 92 is generally aligned with and across from a respective frustoconical passage 82. As best shown by FIG. 7, this arrangement may be achieved by equally spacing each axis 94 of the cylindrical passages 92 in each group 97, 99 a radius r from the axis 84 of the frustoconical passage 82 opposite the group 97, 99. The cylindrical passages 92 in each group 97, 99 may also be equally angularly spaced from each other along a circumference 101 centered on the axis 84 of frustoconical passage 82 opposite the group 97, 99. In an embodiment of the invention, the radius r may be roughly provided by:

$$r \approx \frac{d}{\sqrt{2}}$$

so that adjacent cylindrical passages 92 in each group form a generally cloverleaf pattern, e.g., by being in close proximity, touching, or overlapping.

The distal end 98 of each cylindrical passage 92 may be configured to receive a respective light source 72, which may be mounted to and held in place by a source circuit board 100. The holder 70 may be configured so that when one of the light sources 72 in a group 97, 99 is activated, a beam of light emitted from the proximal end 96 of the respective cylindrical passage 92 traverses the space between the source and detector mounting blocks, enters the wide end 88 of frustoconical passage 82, and illuminates the photodetector 74 opposite the group 97, 99.

A chamber 102 configured to fit in the space 81 between the detector and source mounting blocks 76, 78 may include outer surfaces 104-107, an interior 108, and connectors 112, 114 for fluidically coupling the chamber 102 to the machine supply line 24. At least a portion of the chamber 102 may be made of a transparent material, such as PMP, so that light emitted by the light sources 72 passes through the chamber 102 on its way to the photodetectors 74. The interior 108 of chamber 102 may have a generally cylindrical shape with a diameter $d_2$ sufficient to accommodate the flow of solution 58 through the chamber 102.

Although FIGS. 5-9 depict the optical sensor 14 being used with the chamber 102, it should be understood that in alternative embodiments of the invention, the holder 70 may be configured to pass the light emitted by the light sources 72 through a portion of the machine supply line 24, a glass container, or some other suitable vessel. In another alternative embodiment of the invention, the interior 108 of chamber 102 may be configured so that the machine supply line 24 can be fed through chamber 102. The chamber 102 may thereby be used to locate the machine supply line 24 in the space 81, in which case the connectors 112, 114 may be omitted.

The light sources 72 may include LEDs oriented by a fitting (not shown) configured to aim each LED in a respective group 97, 99 at a fixed point a predetermined distance in front of the group 97, 99, e.g., the focal point 64 of the respective photodetector 74. The fitting may include an aperture or slot that provides an optical window between the LED and the chamber 102. The dimensions of the optical window and the predetermined distance may be selected so that the beam of light 62 emitted by the LED sufficiently illuminates its photodetector 74, and does not provide a significant amount of light to any other photodetectors 74. The LED may be oriented in a dual row configuration with each LED being angled slightly to provide the same maximum intensity and area coverage at a point of focus that aligns a focal point of the beam of light with the face of the photodetector 74.

In an alternative embodiment of the invention, the holder 70 may be assembled from multiple subassemblies, including at least one subassembly for each group 97, 99 of light sources 72. Using subassemblies may facilitate alignment of the light sources 72 with the photodetectors 74 in a mass production environment. For example, having separate subassemblies may enable the location and angle of each group 97, 99 of light sources 72 and/or the photodetector 74 to be adjusted independently so that the locus for the illuminated focal point of the group 97, 99 is located on the corresponding photodetector 74.

Grouping the light sources 72 may address issues caused by the beams of light 62 being refracted differently due to changes in the refraction index of the solution 56, which may change based upon the amount and type of chemical product 18 being added to the diluent 26. The effects of changes in the index of refraction may increase as the lateral offset of the light sources 72 relative to the center of the photodetector 74 increases. Advantageously, grouping the light sources 72 into multiple groups 97, 99 and associating each group 97, 99 with a separate photodetector 74 may minimize the amount of lateral offset between the light sources 72 and their respective photodetector 74.

The sensor control module 12 may be configured to determine a transmission coefficient at each wavelength emitted by the light sources 72 for the corresponding optical path through the solution 58 based on the strength of the signal received from the receiving photodetector 74. Each light source 72 may be characterized over its useful intensity range for the distance of the optical path through the solution 58. A typical distance through the solution 58 may be about 20 mm. Variations in this distance may be compensated for by adjusting the intensity of the light source 72 to offset the optical path attenuation associated with this variation in distance. The sensor control module 12 may set an electrical bias independently for each light source 72 of optical sensor 14 to provide a consistent and repeatable intensity for each light source 72. To this end, the sensor control module 12 may be configured to drive each light source 72 at a level that provides the photodetectors 74 with a generally constant luminous intensity across the light spectrum employed by the optical sensor 14.

The spectral sensitivity of the photodetectors 74 may vary with the wavelength of light received, and may have a similar spectral sensitivity as the human eye. To compensate for this variation in sensitivity, the sensor control module 12 may set the drive level for each light source 72 independently using a baseline calibration process. The drive levels may then be stored in memory 36 along with the corresponding output levels of the photodetector 74 as baseline calibration parameters.

Each drive level may be set to a normalized baseline level that, when the corresponding light source 72 is activated, causes the light source 72 to emit light having an intensity which causes the photodetector 74 to output a signal at a similar level as when the other light sources 72 are activated. Normalizing the baseline drive levels for each light source 72 based on the output of the photodetector 74 under a known condition may enable the photodetector 74 to perform as if it had a relatively flat response across the spectrum utilized by the optical sensor 14. The above baseline calibration process may be performed, for example, with unadulterated diluent 26 (i.e., diluent 26 to which no products 18 have been added) in the chamber 102 to create an array of baseline drive levels that define a normalized drive curve. This drive curve may define the variation in intensity at each wavelength of light used by the optical sensor 14 that equalizes the spectral response of the optical sensor 14. Correcting the spectral response of the photodetector 74 using the normalized drive curve may allow the optical sensor 14 to perform similarly to sensors using more expensive wide-band photodetectors having an intrinsically flat spectral response.

Figure 10:
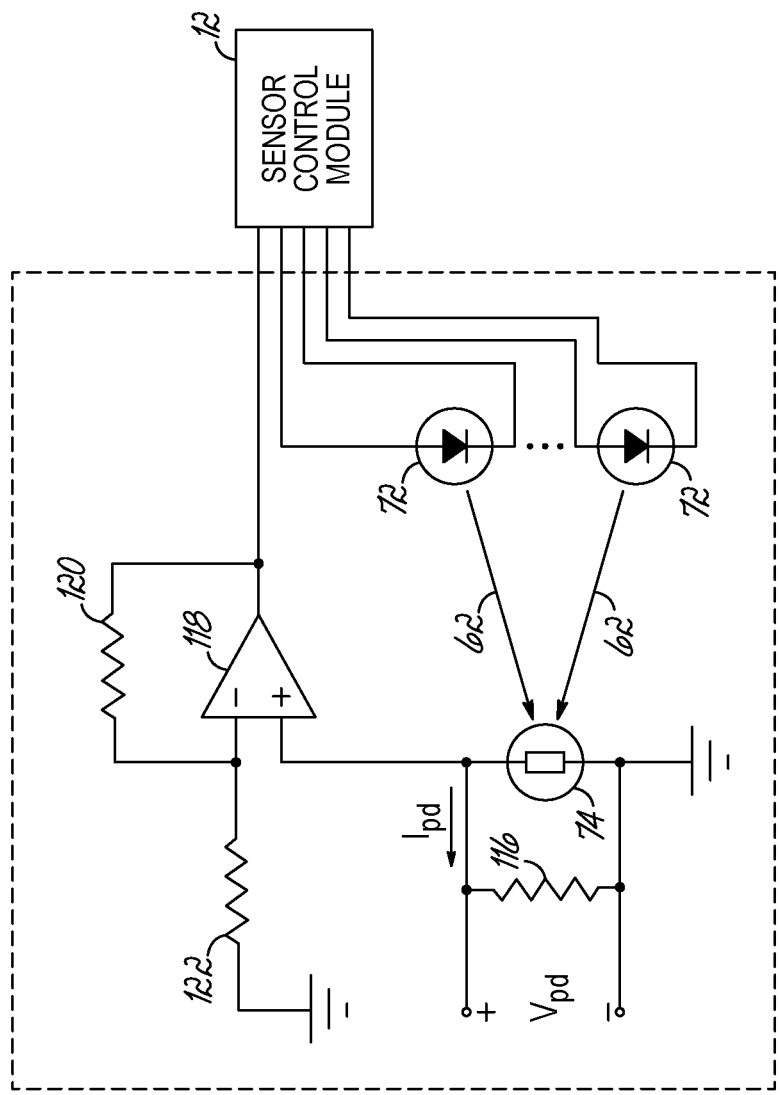
FIG. 10 is a schematic view of an optical sensor in accordance with the optical sensors of FIGS. 1-9 showing details of the light source and photodetector circuits.

Referring now to FIG. 10, each photodetector 74 may be coupled to a load resistor 116 so that the current $I_{pd}$ generated by the photodetector 74 produces a voltage $V_{pd}$ across the load resistor 116. The photo detector voltage $V_{pd}$ may be coupled to the non-inverting input of an operational amplifier 118. The gain of the operational amplifier 118 may be set by a feedback resistor 120 and ground resistor 122 so that the output of the operational amplifier is given by:

$$V_{out} = (I_{pd} \times R_L) \times \left(1 + \frac{R_F}{R_G}\right)$$

where $R_L$ is the resistance of the load resistor 116, $R_F$ is the resistance of the feedback resistor 120, and $R_G$ is the resistance of the ground resistor 122.

The gain of the amplifier may be selected so that the output voltage $V_{out}$ is the maximum voltage that can be handled by the sensor control module 12 (e.g., the maximum voltage for an analog to digital (A/D) port of the processor 34 or I/O interface 38) when the beam of light 62 is in an unattenuated state. The unattenuated state may be determined by providing unadulterated diluent 26 to optical sensor 14 and activating each light source 72 sequentially, thereby causing the optical sensor 14 to output its full voltage at each wavelength λ.

In an alternative embodiment of the invention, the optical sensor 14 may include modulator and/or multiplexer circuitry (not shown) that converts the output voltages $V_{out}$ into signals having a characteristic (e.g., phase, frequency, amplitude, digital value, etc.) that is dependent on $V_{out}$. Encoding the output voltage $V_{out}$ using an analog or digital modulation scheme may enable the optical sensor 14 to provide a signal having an increased resolution and/or that uses fewer connectors to the sensor control module 12 than would be possible with optical sensors 14 lacking this feature.

In operation, the sensor control module 12 may periodically activate each light source 72 and sample the output of the corresponding photodetector 74. The light sources may be activated in sequence, and the data collected from the photodetector 74 may be stored in memory 36, such as in an array. The sensor control module 12 may compare this data to previously stored data that was collected during previous sampling periods and/or calibration processes. Based on this comparison, the sensor control module 12 may determine a level of attenuation for each light source 72. The level of attenuation may vary across the wavelengths of light emitted by the light sources depending on the optical characteristics of the solution in the chamber 102. The attenuation verses wavelength may provide spectroscopic signature that can be used to determine the types and/or concentrations of chemical products in the solution. The interaction between the light emitted by the light sources 72 and the chemicals in the solution as a function of wavelength may be due to the chemistry of the solution. The chemistry of the solution may thereby be accurately determined using spectroscopic principals.

By way of example, solutions having a visible blue tint may attenuate wavelengths in the blue part of the spectrum more than wavelengths in other parts of the spectrum due to the more efficient scattering of blue light by the solution. More efficient scattering at a particular wavelength may cause more light at that wavelength to be reflected away from the optical path of the beam of light 62 so that less of the light reaches the photodetector 74. Solutions may also absorb light differently at different wavelengths depending on their chemistry. This absorption may further affect the transmissive characteristics of the solution and thus the amount of light received by the photodetector 74.

The equation:

$$T = \frac{I_S}{I_C}$$

may be used to quantify the transmissive characteristics of a solution, where T is the transmission coefficient, $I_C$ is the current output by the photodetector 74 with the light source 72 driven at the baseline drive level and unadulterated diluent 26 in the chamber 102, and $I_S$ is the current output by the photodetector 74 during the sampling period. The transmission coefficient T may be a percentage of light transmitted by the solution based on the ratio of the light output by the light source 72 to the amount the of energy the photodetector 74 receives after the beam of light 62 passes through the side walls 104-107 of chamber 102 and the solution 58 in chamber 102.

The transmission coefficient T may be dependent on both the wavelength of light being used and the type and amount of products 18 mixed with the diluent 26. As the level of dilution increases, the characteristics of the solution 58 may change so that the characteristics are closer to the characteristics of unadulterated diluent 26. Typically, unadulterated diluent 26 will have a higher transmission coefficient T than any solution including a chemical product 18, and will thus allow the greatest amount of light to be incident on the photodetector 74.

A chemical channel calibration process may be performed (for example, during setup or maintenance of the chemical dispensing system 10) to determine the spectral characteristics of the working solutions that are to be dispensed by the dispenser 22 while in operation. The chemical channel calibration process may include dispensing or otherwise providing one or more reference solutions to the chamber 102. The reference solution may have at least one known characteristic, e.g., a known level of product 18 or other chemical. While a known reference solution is in the chamber 102, the sensor control module 12 may sequentially drive the light sources 72 using the baseline drive levels and determine the transmission coefficient T at one or more of the wavelengths used by the optical sensor 14. These transmission coefficients T may then be stored in memory 36 as chemical calibration parameters and used to determine if the working solutions being dispensed during operation of the dispensing system 10 have the proper concentrations of chemical products 18.

Advantageously, embodiments of the invention may reduce the cost of characterizing solutions based on their spectral characteristics by using a plurality of monochromatic light sources 72 and photodetectors 74 that cover all or portions of the light spectrum, e.g., light having wavelengths λ between 400 nm and 800 nm. It has been determined that operating in this range of wavelengths provides highly repeatable measurements. The repeatability of the measurements may be due at least in part to a wide spectrum optical signature characteristic of the products 18. In an embodiment of the invention, dyes or other substances having known optical properties when in solution may be added to the products 18 to further enhance the sensitivity of the measurements.

The sensor control module 12 may be in communication with the system controller 30 so that the system controller 30 can track characteristics of the solution 58 being provided to the machine 20 by the dispenser 22. The system controller 30 may thereby verify that the dispenser 22 dispensed solution 58 for the expected duration, and that the solution 58 dispensed had an acceptable concentration of the correct product 18. The sensor control module 12 may also diagnose and provide an indication to the system controller 30 of operational issues with the dispenser 22, such as a low or out of product condition, that a wrong pump or valve was activated, or any other operational issues that may affect the characteristics of the solution 58 being dispensed.

The dispensing run times of a dispense cycle may vary depending upon the application and the product 18 being dispensed. The sensor control module 12 may be configured to take into account the dispensing run time, and determine the transmission coefficient T for each wavelength by sequentially activating the light sources 72 and sampling the output of the respective photodetector 74 during the dispense cycle. This determination may be repeated multiple times during the dispense cycle, and the samples stored in memory 36. The sensor control module 12 and/or system controller 30 may then determine an average value for the transmission coefficient T for each wavelength λ during the dispense cycle. This data may be compared to the chemical calibration parameters determined during the chemical channel calibration process, and/or other dispense cycles.

The above process may indicate the product dilution state as a running average. The system controller 30 may be programmed to alert the user when abnormal concentration levels are detected. In response to detecting a below normal concentration level, the system controller 30 may be configured to run the dispense cycle longer to obtain the correct solution at the machine, e.g., in cases where additional diluent is added to fill the machine 20 after the dispense cycle. The system controller 30 may also be configured to suspend dispense cycles until the issue is corrected in response to detecting repeated low dilution cycles.

In an alternative embodiment of the invention, the detector mounting block 76 may be configured to hold the same number of photodetectors 74 as light sources 72 in a one-on-one configuration. This embodiment of the invention may use a calibration process that normalizes the response of each photodetector 74. Having each light source 72 paired with a dedicated photodetector 74 may increase the complexity of the optical sensor 14 and require more communication ports on the sensor controller module 12. However, a one-to-one relationship between each light source 72 and photodetector 74 may also reduce the difficulty of aligning the light sources 72 to the photodetectors 74 since each light source 72 could be placed directly opposite of its respective photodetector 74. This one-to-one configuration may also allow the sensor controller module 12 to collect data for more wavelengths simultaneously than would be possible with fewer photodetectors 74.

The HMI 32 of sensor control module 12 may be configured to display data in a graphical format to provide the user with a quick visual indication of the current dispense cycle. This data may also be displayed by the system controller 30. In either case, the display may comprise a simple bar graph or text that shows a percentage concentration level, which may be based on a comparison between the sampled transmission coefficient T and the stored calibration parameters. The indication may also be as simple as illuminating a single compliance indicator LED when the detected concentration levels are within a given percentage of the reference solutions or a certain amount of product 18 has been provided to the machine 20.

The sensor control module 12 may communicate using a local or wide-area network and/or the Internet, for example, to provide data related to the solutions being dispensed. This data may be provided to local users through an application on a smartphone or wireless tablet, or to remote users through a gateway device. The data may include any alerts (such as diagnostic, system, temperature, power, etc.) that the dispensing system 10 is configured to report.

Embodiments of the invention may be used in conjunction with electrical conductivity measurement circuitry, such as admittance detectors, to provide another reference point for additional verification of the characteristics of dispensed solutions and the duration of dispense cycles. Using optical transmission and electrical conductivity analysis methods in tandem may provide a comprehensive analytical process for determining types of solutions being dispensed, timing of dispense cycles, and concentrations of product in the solution that was dispensed.

In general, the routines executed to implement the embodiments of the invention, whether implemented as part of an operating system or a specific application, component, program, object, module or sequence of instructions, or a subset thereof, may be referred to herein as "computer program code," or simply "program code." Program code typically comprises computer-readable instructions that are resident at various times in various memory and storage devices in a computer and that, when read and executed by one or more processors in a computer, cause that computer to perform the operations necessary to execute operations and/or elements embodying the various aspects of the embodiments of the invention. Computer-readable program instructions for carrying out operations of the embodiments of the invention may be, for example, assembly language or either source code or object code written in any combination of one or more programming languages.

Various program code described herein may be identified based upon the application within which it is implemented in specific embodiments of the invention. However, it should be appreciated that any particular program nomenclature which follows is used merely for convenience, and thus the invention should not be limited to use solely in any specific application identified and/or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer-readable storage medium having computer-readable program instructions thereon for causing a processor to carry out aspects of the embodiments of the invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, and/or operations specified in the flow-charts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flow-charts, sequence diagrams, and/or block diagrams.

In certain alternative embodiments, the functions, acts, and/or operations specified in the flow-charts, sequence diagrams, and/or block diagrams may be re-ordered, processed serially, and/or processed concurrently consistent with embodiments of the invention. Moreover, any of the flow-charts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, actions, steps, operations, elements, and/or components, but do not preclude the presence or addition of one or more other features, integers, actions, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. An apparatus for analyzing a liquid, comprising:
   one or more photodetectors;
   a first light source configured to generate a first beam of light that has a first wavelength, passes through the liquid, and illuminates at least one of the one or more photodetectors after passing through the liquid;
   a second light source configured to generate a second beam of light that has a second wavelength different from the first wavelength, passes through the liquid, and illuminates at least one of the one or more photodetectors after passing through the liquid;
   a processor; and
   a memory storing program code that, when executed by the processor, causes the apparatus to:
   when the liquid is a first solution:
      receive a first signal from the one or more photodetectors indicative of a first intensity of the first beam of light,
      receive a second signal from the one or more photodetectors indicative of a second intensity of the second beam of light,
      determine a first transmission coefficient based on the first intensity, and
      determine a second transmission coefficient based on the second intensity;
   when the liquid is a second solution:
      receive a third signal from the one or more photodetectors indicative of a third intensity of the first beam of light,
      receive a fourth signal from the one or more photodetectors indicative of a fourth intensity of the second beam of light,
      determine a third transmission coefficient based on the first intensity, and
      determine a fourth transmission coefficient based on the fourth intensity;
   determine a first difference between the first transmission coefficient and the third transmission coefficient;
   determine a second difference between the second transmission coefficient and the fourth transmission coefficient; and
   determine a characteristic of the first solution based on the first difference and the second difference.

2. The apparatus of claim 1 further comprising:
   a chamber configured to receive the liquid so that the first and second beams of light pass through the liquid in the chamber.

3. The apparatus of claim 2 wherein the chamber includes at least a portion of a machine supply line.

4. The apparatus of claim 2 wherein the chamber includes a connector configured to couple the chamber to a machine supply line.

5. The apparatus of claim 1 wherein the program code is further configured to cause the apparatus to:
   sequentially activate the first light source and the second light source, the first signal being received in response to activating the first light source, and the second signal being received in response to activating the second light source.

6. The apparatus of claim 1 wherein the characteristic is a type of a chemical product in the liquid, a concentration of the chemical product in the liquid, or both the type and the concentration of the chemical product in the liquid.

7. The apparatus of claim 1 wherein the first solution is a working solution, and the second solution is a reference solution having a known characteristic.

8. The apparatus of claim 1 wherein the first solution is one of a working solution or a reference solution, the second solution is an unadulterated diluent, and the program code further causes the apparatus to:
   store the third intensity as a first baseline calibration parameter in the memory; and
   store the fourth intensity as a second baseline calibration parameter in the memory,
   wherein the first transmission coefficient is determined by comparing the first intensity to the first baseline calibration parameter, and
   the second transmission coefficient is determined by comparing the second intensity to the second baseline calibration parameter.

9. A method of analyzing a liquid, comprising:
   when the liquid is a first solution:
      passing a first beam of light having a first wavelength through the liquid, measuring a first intensity of the first beam of light after passing through the liquid, determining a first transmission coefficient based on the first intensity, passing a second beam of light having a second wavelength different from the first wavelength through the liquid, measuring a second intensity of the second beam of light after passing through the liquid, and determining a second transmission coefficient based on the second intensity;

when the liquid is a second solution:

passing the first beam of light through the liquid, measuring a third intensity of the first beam of light after passing through the liquid, determining a third transmission coefficient based on the third intensity, passing the second beam of light through the liquid, measuring a fourth intensity of the second beam of light after passing through the liquid, and determining a fourth transmission coefficient based on the fourth intensity;

determining a first difference between the first transmission coefficient and the third transmission coefficient;

determining a second difference between the second transmission coefficient and the fourth transmission coefficient; and determining a characteristic of the first solution based on the first difference and the second difference.

10. The method of claim 9 wherein the first solution is a working solution, and the second solution is a reference solution having a known characteristic.

11. The method of claim 10 further comprising:

storing the third and fourth transmission coefficients in a memory as chemical calibration parameters.

12. The method of claim 9 wherein the characteristic of the liquid is a type of a chemical product in the liquid, a concentration of the chemical product in the liquid, or both the type and the concentration of the chemical product in the liquid.

13. The method of claim 9 wherein the first solution is one of a working solution or a reference solution, the second solution is an unadulterated diluent, and further comprising:

setting a first baseline calibration parameter based to the third intensity; and setting a second baseline calibration parameter based on the fourth intensity, wherein the first transmission coefficient is determined by comparing the first intensity to the first baseline calibration parameter, and the second transmission coefficient is determined by comparing the second intensity to the second baseline calibration parameter.

14. The method of claim 9 wherein the first intensity and the second intensity are measured using a single photodetector.

15. The method of claim 9 wherein the first beam of light and the second beam of light are passed through the liquid sequentially.

16. The method of claim 9 further comprising:

receiving the liquid in a chamber, wherein the first beam of light and the second beam of light are passed through the liquid in the chamber.

17. A computer program product for analyzing a liquid, the computer program product comprising:

a non-transitory computer-readable storage medium; and program code stored on the non-transitory computer-readable storage medium that, when executed by one or more processors, causes the one or more processors to:

when the liquid is a first solution:

pass a first beam of light having a first wavelength through the liquid, measure a first intensity of the first beam of light after the first beam of light has passed through the liquid, determine a first transmission coefficient based on the first intensity, pass a second beam of light having a second wavelength different from the first wavelength through the liquid, measure a second intensity of the second beam of light after the second beam of light has passed through the liquid, and determine a second transmission coefficient based on the second intensity;

when the liquid is a second solution:

pass the first beam of light through the liquid, measure a third intensity of the first beam of light after passing through the liquid, determine a third transmission coefficient based on the third intensity, pass the second beam of light through the liquid, measure a fourth intensity of the second beam of light after passing through the liquid, and determine a fourth transmission coefficient based on the fourth intensity;

determine a first difference between the first transmission coefficient and the third transmission coefficient;

determine a second difference between the second transmission coefficient and the fourth transmission coefficient; and determine a characteristic of the first solution based on the first difference and the second difference.

* * * * *